United States Patent [19]
Klein

[11] Patent Number: 5,829,590
[45] Date of Patent: Nov. 3, 1998

[54] BOX FOR THE STORAGE AND STERILIZATION OF PLURAL DENTAL POSTS AND ASSOCIATED DRILL BITS

[76] Inventor: Philip B. Klein, 744 Mount Pleasant Rd., Bryn Mawr, Pa. 19010

[21] Appl. No.: 841,827

[22] Filed: May 6, 1997

Related U.S. Application Data

[60] Provisional application No. 60/017,855 May 8, 1996.

[51] Int. Cl.$^6$ .......................... A61B 19/02; B65D 85/24; A47F 7/00
[52] U.S. Cl. .......................... 206/369; 206/635; 206/379; 206/383; 206/443; 211/69; 211/70.6
[58] Field of Search ..................................... 422/297, 300; 211/69, 70.6; 206/369, 63.5, 379, 383, 382, 443; 433/77

[56] References Cited

U.S. PATENT DOCUMENTS

| | | | |
|---|---|---|---|
| 1,135,625 | 4/1915 | Savin | 211/69 X |
| 1,973,222 | 9/1934 | Moore | 206/369 |
| 2,962,154 | 11/1960 | Falk | 206/379 |
| 2,971,637 | 2/1961 | Simons | 206/369 |
| 4,306,862 | 12/1981 | Knox | 433/77 |
| 4,503,972 | 3/1985 | Nelligan et al. | 206/379 |
| 5,071,346 | 12/1991 | Domaas | 433/77 |
| 5,129,578 | 7/1992 | Eidsmoe et al. | 211/69 X |
| 5,358,112 | 10/1994 | Gardner | 206/369 |
| 5,453,010 | 9/1995 | Klein . | |
| 5,507,643 | 4/1996 | Klein . | |

*Primary Examiner*—Bryon P. Gehman
*Attorney, Agent, or Firm*—Gregory J. Gore

[57] ABSTRACT

A box for holding a plurality of dental posts and drill bits. The box is formed of a sterilizable material, i.e., stainless steel, and has a pair of end walls, a bottom wall and opposed open sidewalls. A pivotable cover is provided on the box over the bottom wall. A pair of plates are located within the interior of the box and include plural openings therein into which the dental posts and drill bits are extended. When the drill bits and dental posts are in position within the holes in the plates and the box's cover is closed, they are prevented from falling out of the box. The open sides of the box enable the posts and bits to be sterilized within the box by merely placing the box within a sterilizing environment, e.g., within the interior of an autoclave.

6 Claims, 2 Drawing Sheets

BOX FOR THE STORAGE AND STERILIZATION OF PLURAL DENTAL POSTS AND ASSOCIATED DRILL BITS

Priority of this application based upon Provisional patent application, entitled "Box for the Storage and Sterilization of Plural Dental Posts and Associated Drill Bits", filed on May 8, 1996, Ser. No. 60/017,855, is hereby claimed.

FIELD OF THE INVENTION

This application relates generally to storage boxes for dental instruments and more particularly to boxes for dental posts and associated drill bits.

BACKGROUND OF THE INVENTION

Various dental posts are commercially available for preparing a dental restoration from a prepared tooth stub. In some cases such posts are sold as components of a kit including various sized drill bits for drilling a bore into the tooth stub which is to receive the restoration. One particularly useful dental post for a dental restoration is the subject of U.S. Pat. No. 5,453,010 issued to Klein, and is presently being sold by Dental Logics, Inc. under the trademark INTEGRA POST. In particular, such posts are being sold as part of a kit, which itself is the subject of U.S. Pat. No. 5,507,643 issued to Klein. That kit also includes a tool for carrying a selected post into the bore which has been drilled into the tooth stub for which the dental restoration is intended.

A need presently exists for a box to securely hold a plurality of dental posts and associated drill bits so that they are readily available for use when needed. Moreover, such a box should be constructed to ensure that the posts and drill bits cannot accidentally fall out of the box if it is tilted, jostled, dropped, or inverted. Lastly, it is desirable that the posts and bits be sterilizable without requiring their removal from the box, e.g., the box be constructed so that it can be placed in an autoclave to sterilize all the posts and drill bits in a single operation.

SUMMARY OF THE INVENTION

In order to fulfill the needs in the arts, the present invention has been devised. The dental instrument holder of the present invention forms a box having a hinged cover at the top, movable between open and closed positions. The box has open sides and a horizontally-disposed upper plate affixed between front and rear panels of the box. The upper plate has a first portion with a first group of holes therethrough. The box holds a plurality of dental posts, each post having a flange and a shank of reduced diameter removably positioned in the first group of the holes. The first group of holes have diameters greater than the diameter of the shanks of the posts, but less than the diameter of the flanges such that the flanges rest against the upper plate when stored. The first portion of the upper plate is located a distance below the cover when it is closed such that the height of heads of the dental posts is approximately the same as the distance below the cover. The upper plate further includes a second portion having a second group of holes for holding drill bits, each drill bit having a shank and a flange. The second group of holes is greater in diameter than the drill bit shanks.

The instrument holder further includes a lower plate parallel to the upper plate having a third group of holes in a front portion thereof in vertical alignment with the second group of holes in the second portion of the upper plate. The third group of holes in the lower plate receive the burrs of the drill bits and are smaller than the diameter of shanks. Thus, when the drill bits are placed through the aligned holes from above the upper plate, their flanges will be disposed against the lower plate, while their shanks will be restrained from tipping by walls of the second group of holes in the upper plate. The distance between the surface of the lower plate in the region surrounding the third group of holes and inside of the cover when it is closed is approximately equal to but less than the height of the shanks of the drill bits.

The lower plate also includes a stepped-down rear portion directly beneath the first group of holes in the upper plate such that the distance between the first group of holes and the rear portion is greater than the length of the shanks of the dental posts. The cover is hingeably affixed to the top edge of the rear panel and is held closed by a snap-fit connection with the front panel. The upper and lower plates extend the entire width of the front and rear panels and the entire box is preferably formed of stainless steel.

It is therefore an object of the present invention to provide a holder for a plurality of dental posts and associated drill bits so that they are readily available for use. It is a further object of the present invention to construct a holder for dental posts and drill bits such that the posts and bits cannot accidentally fall out of the holder. Finally, it is yet a further object of the present invention to form a holder for dental instruments in the shape of a box which can securely hold posts and drill bits such that they may be sterilizable without requiring their removal from the box. Other objects and many attendant features of this invention will become readily appreciated as the same becomes better understood by reference to the following detailed description when considered in connection with the accompanying drawing.

DETAILED DESCRIPTION OF THE PREFERRED EMBODIMENT

Figure 1:
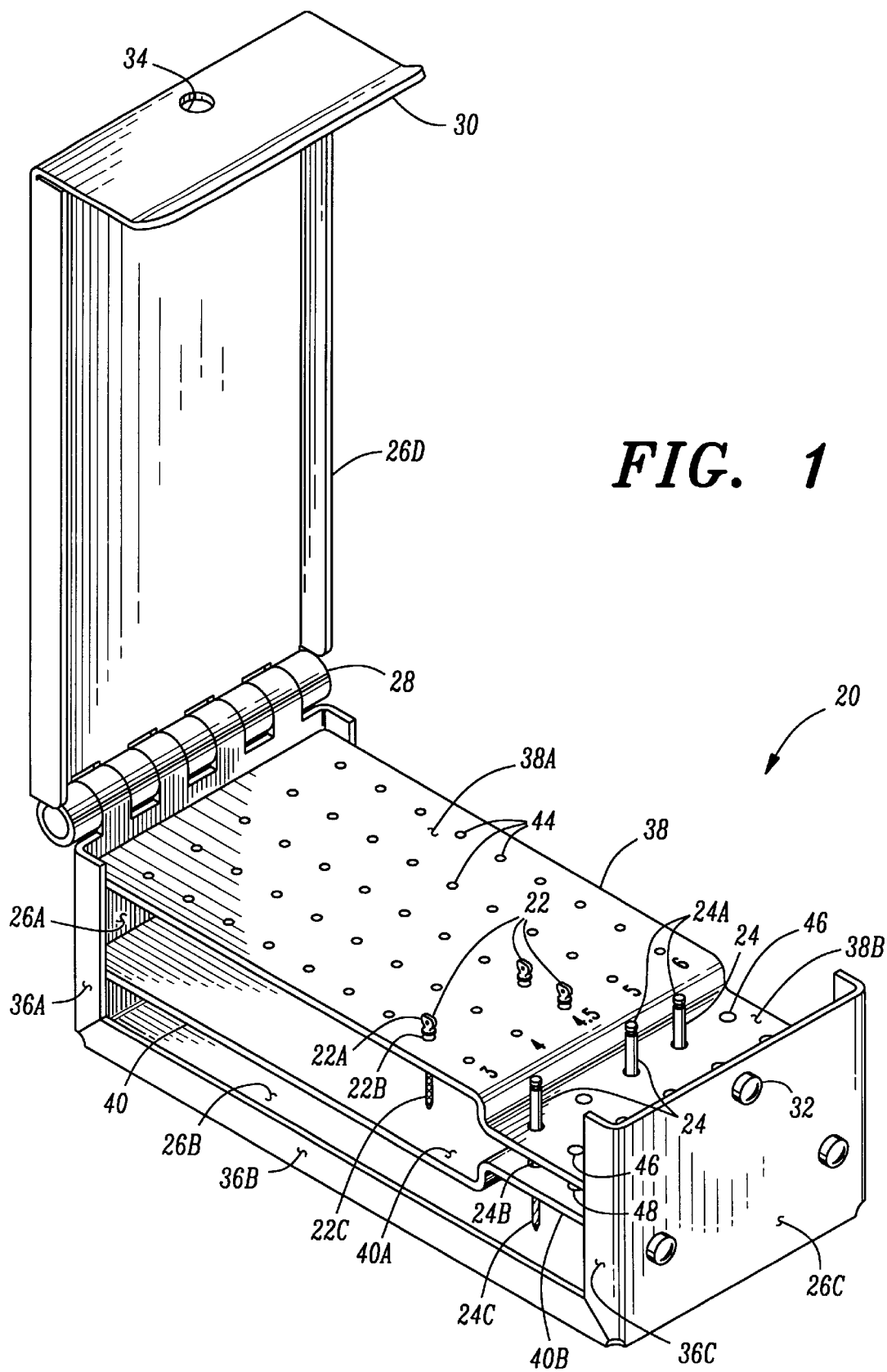
FIG. 1 is a top left front isometric view of the box of the present invention shown with its cover open.

Referring now to the drawing where like reference numerals refer to like parts, in FIG. 1 there is shown a box 20, constructed in accordance with this invention. The box is arranged to hold a plurality of dental posts 22 of varying sizes, and a plurality of drill bits 24 of varying sizes. The drill bits correspond in size to the dental posts and are color coded to ensure that the appropriate drill bit is used for the selected size dental post. Preferably, the dental posts are constructed in accordance with the teachings of the aforementioned U.S. Pat. No. 5,453,010, whose disclosure is incorporated by reference herein, but other types of dental posts can be used as well. Thus, each post includes a head 22A having a flange 22B on the bottom thereof and a fluted cutting tip 22C projecting downward from the shank.

The box 20 is constructed of a strong, sterilizable material, e.g., stainless steel, and basically comprises a body including a rear panel 26A, a base wall 26B, and a front panel 26C. A cover 26D is secured to the top edge of the rear panel 26A by a hinge 28. The cover 26D includes a flange 30 at its end which is arranged to snap over the top edge of the front panel 26C when the cover is closed. A domed detent or projection 32 is provided on the outer surface of front panel 26C adjacent the top to fit into a hole 34 in the flange 30 to lock the cover in place against accidental disconnection, but will enable the flange to be released from the end wall so that the cover can be pivoted back to expose the interior of the box as shown in FIG. 1.

Both right and left sides of the box 20 are open, except for small peripheral flanges 36A, 36B, and 36C extending from the rear panel 26A, the base wall 26B, and the front panel 26C, respectively.

A pair of plates 38 and 40 extend within the box from the inside of the rear panel 26A to the inside of the front panel 26C, and each plate is of the full width of the box, i.e., each plate extends from side to side in the box. The upper plate 38 includes a first portion 38A disposed contiguous with the rear panel 26A and extending for a major length of the box, and a lowered ledge or off-set portion 38B contiguous with the opposite end wall. A plurality of holes are provided in the upper plate, with one group of holes 44 being arranged in plural rows in the plate portion 38A, and with another group 46 being arranged in plural rows in the plate portion 38B. The lower plate 40 includes a rear portion 40A disposed contiguous with the rear panel 26A and extending for a major length of the box, and a raised front portion 40B contiguous with the rear panel end wall. One group of plural holes 48 are provided in plural rows in the front portion of the lower plate 40B and those holes are aligned with the holes 48 in the upper plate portion 38B.

Figure 2:
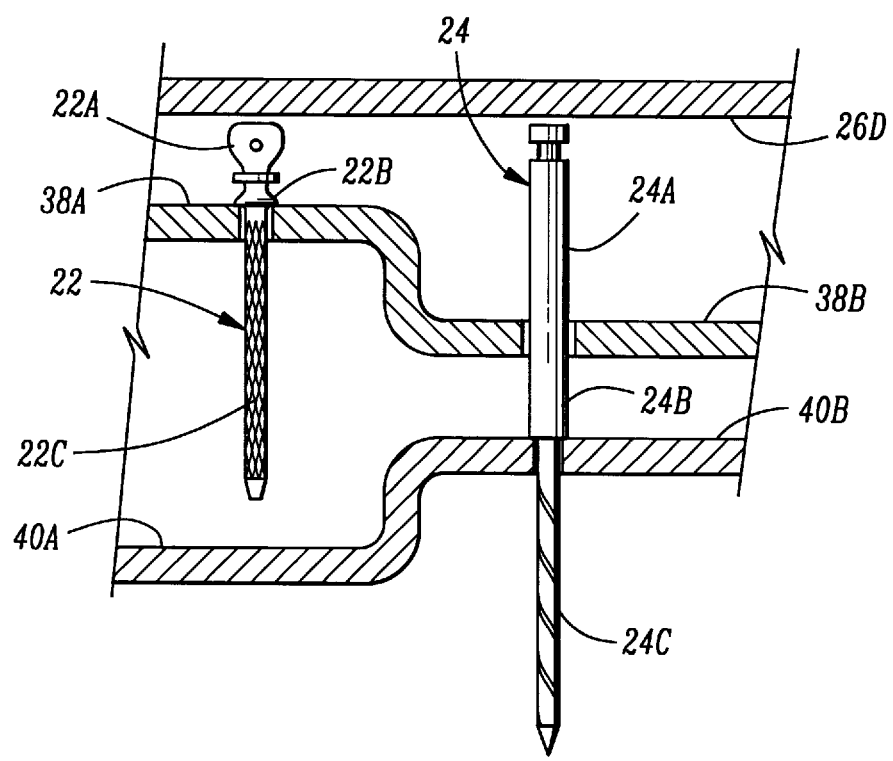
FIG. 2 is a partial left side sectional view taken from FIG. 1 as shown in that figure.

Referring now to FIG. 2, the spacing between the portions 38B and 40B of the upper and lower plates, respectively, is such that when the cutting ends 34C of the drill bits are extended through the aligned holes with their flanges 24B disposed on the bottom plate portion 40B, they will be maintained in an orientation perpendicular to the plane of the bottom wall and the cover. Thus, the drill bits will be prevented from swinging even if the box is jostled. The dental posts are extended through the holes 44 in the upper plate so that their flanges 22B rest on the upper plate portion 38A, but with the bottom of their shanks located above the lower plate rear portion 40A.

The height of the heads 22A of the dental posts is approximately the same as the spacing between the upper plate portion 38A and the inner surface of the cover 26D when the cover is closed. In a similar manner, the height of the shanks 24A of the drill bits is the same as the spacing between the lower plate portion 40B and the inner surface of the cover 26D when the cover is closed. Thus, when the posts and drill bits are in place and the cover is closed, they cannot fall out of the box, i.e., their top end surface is disposed immediately adjacent the inner surface of the closed cover.

Since the box's sides are open, the box can be placed into an autoclave or any other sterilizing apparatus so that all of the drill bits and dental posts can be sterilized at the same time. Once the posts and drill bits are sterilized, the box can be removed from the sterilizing apparatus and is ready to be either stored or opened to enable removal of the posts and/or bits, as the case may be.

It should be understood that the above description discloses specific embodiments of the present invention and are for purposes of illustration only. There may be other modifications and changes obvious to those of ordinary skill in the art that fall within the scope of the present invention which should be limited only by the following claims and their legal equivalents.

What is claimed is:

1. A holder for dental instruments, comprising:

a box having a hinged cover at a top movable between open and closed positions, said box having open sides;

a horizontally-disposed upper plate affixed between front and rear panels of said box, said plate having a first portion with a first group of holes all of the same diameter therethrough;

a plurality of dental posts, each post having a flange and a shank of reduced diameter removably positioned in the first group of said holes, said first group of holes having a diameter greater than the diameter of said shanks of said posts, but less than the diameter of said flanges such that said flanges rest against said upper plate; and wherein said main portion of said upper plate is located a first distance below said cover when closed such that the height of heads of the dental posts is approximately the same as but less than said first distance;

wherein said upper plate further includes a second portion having a second group of holes for holding drill bits, each drill bit having a shank and a flange, wherein said second group of holes all of the same diameter are of greater diameter than the shanks of the drill bits;

a lower plate parallel to said upper plate having a third group of holes in a front portion thereof in vertical alignment with said second group of holes in said second portion of said upper plate and wherein the third group of holes in said lower plate are smaller than the diameter of the shanks of the drill bits, such that when the drill bits are placed through the second group of holes from above the upper plate, their flanges will be disposed against the lower plate, while their shanks will be restrained from tipping by walls of said second group of holes in the upper plate;

wherein said second portion of said upper plate is stepped-down with regard to said first portion of said upper plate; and wherein the lower plate includes a stepped-down rear portion directly beneath said first group of holes in said upper plate such that the distance between said first group of holes and said rear portion is greater than the length of said shanks of said dental posts.

2. The holder of claim 1, wherein said cover is hingeably affixed to the top edge of the rear panel.

3. The holder of claim 2, wherein said cover is held closed by a snap-fit connection with said front panel.

4. The holder of claim 3, wherein said upper and lower plates extend the entire width of said front and rear panels.

5. The holder of claim 4, wherein said holder is formed of stainless steel.

6. The holder of claim 1, wherein the distance between the top surface of the lower plate in the region surrounding the third group of holes and inside of the cover when it is closed is approximately equal to but less than the height of said shanks of said drill bits.

* * * * *